United States Patent
Brown et al.

(10) Patent No.: US 11,395,700 B2
(45) Date of Patent: Jul. 26, 2022

(54) FIBER TIP PROTECTIVE STRUCTURE WITH SCALE INDICATOR

(71) Applicants: Joe D. Brown, Panama City Beach, FL (US); Daniel Malphurs, Panama City Beach, FL (US); Howard S. Klymas, Panama City Beach, FL (US)

(72) Inventors: Joe D. Brown, Panama City Beach, FL (US); Daniel Malphurs, Panama City Beach, FL (US); Howard S. Klymas, Panama City Beach, FL (US)

(73) Assignee: OPTICAL INTEGRITY, INC., Panama City Beach, FL (US)

( * ) Notice: Subject to any disclaimer, the term of this patent is extended or adjusted under 35 U.S.C. 154(b) by 597 days.

(21) Appl. No.: 16/414,255

(22) Filed: May 16, 2019

(65) Prior Publication Data

US 2020/0069371 A1   Mar. 5, 2020

Related U.S. Application Data

(60) Provisional application No. 62/672,143, filed on May 16, 2018.

(51) Int. Cl.
| | | |
|---|---|---|
| *G02B 6/00* | (2006.01) | |
| *A61B 18/22* | (2006.01) | |
| *A61M 25/01* | (2006.01) | |
| *G02B 6/44* | (2006.01) | |

(52) U.S. Cl.
CPC ......... *A61B 18/22* (2013.01); *A61M 25/0108* (2013.01); *G02B 6/443* (2013.01); *A61B 2018/2222* (2013.01); *A61B 2018/2255* (2013.01)

(58) Field of Classification Search
CPC ............ A61B 18/22; A61B 2018/2222; A61B 2018/2255; A61M 25/0108; G02B 6/443
USPC ...... 385/38, 60–62, 66–68, 81, 84, 116–118, 385/133–134
See application file for complete search history.

(56) References Cited

U.S. PATENT DOCUMENTS

| | | |
|---|---|---|
| 9,678,275 B1 | 6/2017 | Griffin |
| 2008/0188843 A1 | 8/2008 | Appling et al. |
| 2009/0292278 A1 | 11/2009 | Lewinsky et al. |
| 2013/0218147 A1 | 8/2013 | Brown |
| 2013/0345686 A1 | 12/2013 | Brown |
| 2014/0316397 A1 | 10/2014 | Brown |
| 2016/0106501 A1* | 4/2016 | Appling ................. A61B 18/22 606/15 |
| 2017/0042618 A1 | 2/2017 | Brown |

FOREIGN PATENT DOCUMENTS

WO     2017192869 A1     11/2017

* cited by examiner

*Primary Examiner* — Kaveh C Kianni
*Assistant Examiner* — Hung Q Lam
(74) *Attorney, Agent, or Firm* — Bacon & Thomas, PLLC

(57) ABSTRACT

A protective structure for the distal treatment end of a surgical laser fiber inserted into a patient through a scope includes uniformly-spaced ruler or scale markings that are visible through the scope and that enable the size of an object within the field of view of the scope to be precisely determined.

19 Claims, 1 Drawing Sheet

FIBER TIP PROTECTIVE STRUCTURE WITH SCALE INDICATOR

This application claims the benefit of provisional U.S. Patent Appl. Ser. No. 62/672,143, filed May 16, 2018, incorporated herein by reference.

BACKGROUND OF THE INVENTION

1. Field of the Invention

The invention relates to the field of laser surgery, and in particular to the modification of fiber tip protective structures to include scale-indicating markings such as ruler or scale lines that enhance the ability to determine the scale of tissue or objects near the fiber tip.

The fiber tip protective structures to which the scale-indicating markings are applied may include caps, ferrules, sleeves, sheaths, standoff catheters, or any other protective structures that are placed over the distal or treatment end a surgical laser optical fiber, or into which the end of the surgical fiber is inserted, to (a) protect the fiber tip and/or a scope through which the fiber is inserted, (b) prevent erosion of the fiber tip, (c) enable the formation of an air bubble to reduce beam attenuation during laser lithotripsy (aka the Moses effect), and/or (d) any other purpose.

2. Description of Related Art

The term surgical laser fiber refers to an optical fiber through which laser energy is delivered to a target, such as a tissue or stone, during a surgical procedure. The present invention concerns surgical procedures that take place within the body of the patient, the optical fiber being inserted through a scope that permits the operator to view the distal end of the fiber and the target in order to observe and control treatment. The fiber itself typically includes a core, one or more cladding layers, and one or more buffer layers surrounded by a jacket. Each of the core, cladding, and buffer layers typically extends along the entire length of the fiber, with the except of proximal and distal ends that may be stripped of the jacket and one or more buffer layers.

The fiber tip protective structures to which the invention relates surround the distal end of the fiber, and are typically fixed to either the jacket or fiber buffer to serve varied purposes such as preventing contact between the fiber tip and a target tissue or stone, preventing damage to the scope during insertion of the fiber, reducing fiber tip erosion prevention, and/or maintenance of an air passage between the fiber tip and the target to provide a Moses effect. The protective structures may be used with forward firing fibers, or fibers that are arranged to apply the treatment radiation radially or at an angle to the axis of the fiber.

In the embodiment of the present invention illustrated herein, fiber tip protective structures are soft tips or ferrules or the type described in the inventor's PCT Publication No. WO 2017/192869, U.S. Patent Publication No. 2013/0345686, and Provisional Patent Appl. Ser. No. 62/648,108, filed Mar. 26, 2018; each of which discloses standoff fiber tips that serve to maintain a minimum distance between the distal end of the fiber and a stone during a laser lithotripsy procedure. However, the invention is not limited to the specific types of standoff fiber tip or ferrule disclosed in PCT Publication No. WO 2017/192869 and copending U.S. Patent Publication No. 2013/0345686. Instead, the principles of the invention may be applied to any protective structure that is positioned near or secured to at least the distal end of the fiber during a laser surgery procedure, including the protective sleeves for side or forward firing fibers disclosed in the inventor's U.S. Patent Publication No. 2017/0042618, as well as the protective caps or ferrules described in U.S. Patent Publication Nos. 2009/0292278 (Lewinsky et al.) and 2008/0188843 (Appling), U.S. Pat. No. 9,678,275 (Griffin), and the article by Hutchens et al. entitled "*Hollow Steel Tips for Reducing Distal Fiber Burn-Back During Thulium Fiber Laser Lithotripsy*," in *Journal of Biomedical Optics*, Vol. 18(7), July 2013.

By way of background, it is known from the inventor's U.S. Patent Publication No. 2014/0316397 to provide markings on the proximal end of the fiber, i.e., the end into which the laser energy is injected as opposed to the distal end which is positioned at the treatment site. The purpose of these marking is to enable the position of the distal end to be estimated based on the position of the proximal end, after insertion of the fiber into a sheath and/or a scope. Because of fiber tip erosion, however, the markings at the proximal end do not provide an accurate indication of the position of the fiber tip. This can be alleviated to a degree by providing cut lines at the distal end, as also disclosed in U.S. Patent Publication No. 2014/0316397, so that the fiber can be repeatedly trimmed to correspond to lines at the proximal end. However, as disclosed in the above cited PCT Publication No. WO 2017/192869 and other patent publications of the inventor, the use of erosion-preventing tips, caps, sleeves, or the like eliminates the need for repeated trimming of the fiber, and therefore for cut lines at the distal end of the fiber. Furthermore, as disclosed in the inventor's PCT publication, in cases where the protective structure extends beyond the end of the fiber, the distal end of the fiber can be positioned precisely relative to the target by maintaining contact between the fiber tip protective structure and the target. As a result, the use of fiber tip protective structures can eliminate the need for, or usefulness of, markings applied to the distal end of the fiber itself.

It is also known to provide markings at the distal end of a protective sheath that extends the entire length of the fiber, and that is locked to the scope at the proximal end after insertion of the fiber into the sheath and the sheath into the scope, as disclosed in the inventor's U.S. Patent Publication No. 2013/0218147. These markings are solely for the purpose of providing cut lines that enable the length of the sheath to be matched to the length of the scope, and therefore are neither uniform nor usable as ruler or scale lines for the purposes of the present invention.

One problem not addressed in any of the above-cited publications and patent documents is the difficulty in assessing the size of targets viewed through the scope. The size of the target can be a critical factor in deciding whether to proceed with or terminate a surgical procedure before the laser radiation is applied. For example, it would be advantageous if the size of a stone could be determined by observing the stone in relation to a marked standard. This would allow the clinician to delay or terminate a treatment procedure if a stone present in the urinary tract of a patient turned out to be sufficiently small to be treated using non-surgical options, and therefore with a lower risk of pain or complications.

SUMMARY OF THE INVENTION

The invention relates to a fiber tip protective structure with a ruler in the form of scale-indicating markings applied to the protective structure. In the illustrated embodiments, the markings are ruler or scale lines having a predetermined spacing, but it will be appreciated that other markings may be used to indicate scale, including dashes, dots, or other images or shapes.

For optimal visibility, the scale-indicating markings or reference lines of the invention can be applied to an outside surface of a transparent end section of a protective cap or ferrule fixed to the tip of the optical fiber, for example a cap or ferrule of the type disclosed in the above-cited Provisional Patent Appl. Ser. No. 62/648,108. It is also within the scope of the invention to apply the scale-indicating markings to an inside surface or to embed the scale-indicating markings within the transparent material of the cap or ferrule, to apply the scale-indicating markings to the outside surface of an opaque protective structure, or to provide radio opaque markings visible under diagnostic imaging.

In the illustrated embodiment, an exemplary spacing for the ruler or scale lines is 500 micrometers (0.5 millimeters), although the spacing may be varied without departing from the scope of the invention, for example within a range of on the order of (or approximately) 100 micrometers to on the order of (or approximately) one millimeter, depending on the surgical application or treatment procedure in which the fiber tip protective structure is used.

While the spacing of the ruler or scale lines should be uniform in order to enable the size of targets to be determined, the width of the lines applied to a protective structure may be varied. For example, the ruler or scale lines may be optionally made up of alternating thick and thin bands to more easily maintain reference points with respect to the tip of the protective structure, or (d) optionally including an extra wide band for extra visibility and fiber tip alignment in the operating field, as provided in the exemplary embodiment of the invention.

Although one preferred example of a protective structure is illustrated, the ruler or scale lines of the invention may be applied to any protective structure that at least surrounds the distal end of the fiber, including a variety of caps or ferrules fixed to the fiber jacket or buffer and extending over a stripped section of the fiber so as to prevent contact between the fiber and surrounding tissues and protect the scope from damage as the fiber is inserted into the scope. Alternative protective structures to which the ruler or scale lines may be applied include, by way of example and not limitation, soft tips, disposable tips, standoff tips, sleeves, sheaths, and catheters, including structures that are fixed to the end of the fiber and protective structures within which the fiber is movable during a treatment procedure, and protective structures for both side and forward firing fibers.

To enhance the visibility of the markings, and their use as a reference for the size of objects adjacent the protective structure within the field of view of the operator, the markings may include bands of varying thickness, including an extra wide band for extra visibility and fiber tip alignment in the operating field.

DETAILED DESCRIPTION OF THE PREFERRED EMBODIMENTS

Throughout the following description and drawings, like reference numbers/characters refer to like elements. It should be understood that, although specific exemplary embodiments are discussed herein there is no intent to limit the scope of present invention to such embodiments. To the contrary, it should be understood that the exemplary embodiments discussed herein are for illustrative purposes, and that modified and alternative embodiments may be implemented without departing from the scope of the present invention.

Figure 1:
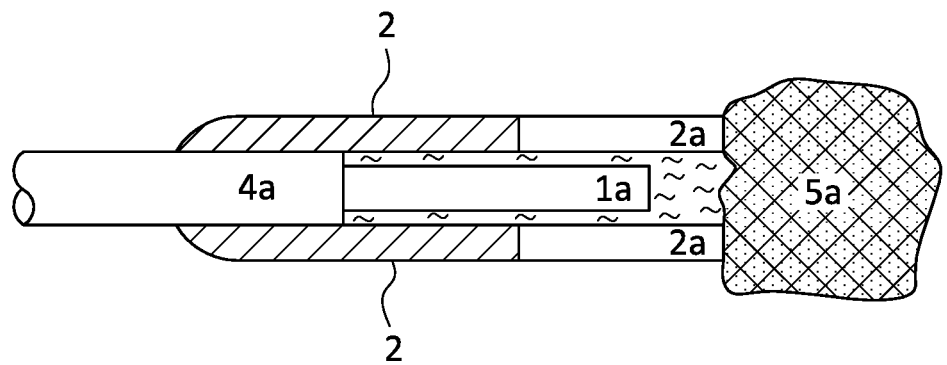
FIG. 1 is a side view showing a fiber tip protective structure with a transparent end section to which the principles of the present invention may be applied.

As illustrated in FIG. 1, a standoff cap or ferrule 2 of the type disclosed in Provisional Patent Appl. Ser. No. 62/648, 108 is fixed to an outer layer of a fiber 41 and surrounds a stripped end section 1a of the fiber. An end section 2a of the cap or ferrule is optionally made of a transparent material that allows off-axis laser radiation to pass without overheating the cap or ferrule. The end section 2a extends forwardly of the fiber tip to provide a standoff that can be positioned against a stone 5a to provide a predetermined spacing between the fiber tip and the stone during a lithotripsy procedure.

Figure 2:
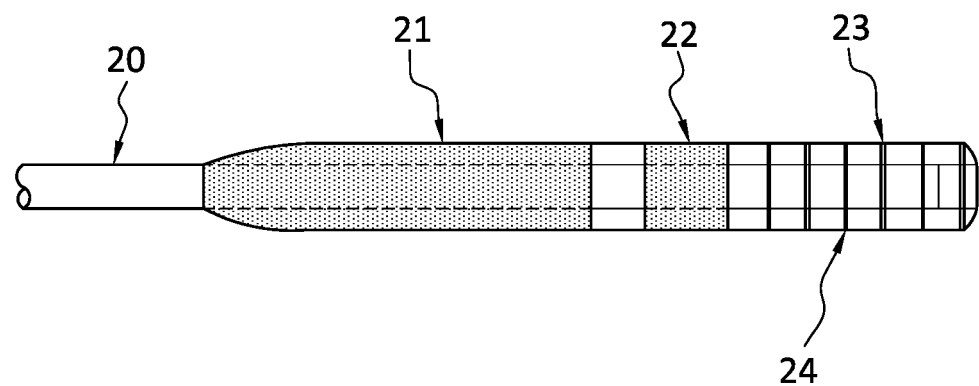
FIG. 2 is a side view of an exemplary embodiment of the invention in which ruler or scale lines have been applied to a protective structure of the type illustrated in FIG. 1.

In the exemplary embodiment of the invention illustrated in FIG. 2, the protective cap or ferrule 21 is fixed to a fiber 20 and the transparent end section is configured with scale-indicating markings in the form of opaque printed bands that are spaced at, for example, uniform increments of 500 micrometers (0.5 millimeters). The bands may have any color that is visible to the operator and may be applied by techniques other than printing on the outside surface of the cap or ferrule, so long as the bands can remain visible through a scope during a treatment procedure. For example, the ruler or scale lines may be applied to an inside surface of the transparent section of the cap or ferrule, embedded within the transparent material, applied to the outside surface of an opaque protective structure, or provided as radio opaque markings visible under diagnostic imaging. In addition, the spacing of the bands may be varied for different types of treatment procedures and possible target sizes, in increments ranging from on the order of 100 micrometers (and possibly smaller) to on the order of (or approximately) one millimeter (and possibly larger), depending on the treatment procedure. Irrespective of the selected spacing, however, the increments should be uniform in order to provide a ruler or scaling effect that allows the relative size of a target to be determined.

In the illustrated embodiment, the band widths alternate between wider bands 23 and narrower bands 24 at each increment, similar to major and minor tick marks on standard measuring devices, in order to easily maintain reference points along the tip. One wide band 22 is depicted for extra visibility and fiber tip alignment in the operating field.

Although illustrated as lines, it will be appreciated that other scale-indicating markings may be substituted for lines. For example, dashes, dots, or other scale indicating shapes or images may be substituted.

By way of example, the printed bands can be used during a lithotripsy operation to estimate stone dimensions. Using the band spacing a length reference, a surgeon may be able to measure a stone and decide if it will pass from the patient's body. The printed bands may also consist of a radio-opaque substance that might be useful under diagnostic imaging.

Although a specific protective structure suitable for stone lithotripsy applications is illustrated, the fiber tip protective structures to which the ruler or scale lines are applied may include caps, ferrules, sleeves, sheaths, standoff catheters, or any other protective structures that are placed over the distal or treatment end a surgical laser optical fiber, or into which the end of the surgical fiber is inserted, for purposes that are not limited to protection of the fiber tip or scope or to lithotripsy applications.

What is claimed is:

1. A fiber tip protective structure that surrounds at least a distal end of a surgical laser fiber, the surgical laser fiber including at least a core, a cladding layer, and one or more buffer layers surrounding the core and cladding layer and extending a length of the fiber, at least one buffer layer being stripped at the distal end, the surgical laser fiber being inserted through a scope to a treatment site and the distal end of the surgical laser fiber being visible through the scope when the distal end is at the treatment site, wherein:
scale-indicating markings are applied to the fiber tip protective structure to enable a size of tissues or objects within a field of view of the scope to be determined, and
the scale-indicating markings are uniformly spaced ruler or scale lines.

2. A fiber tip protective structure as claimed in claim 1, wherein the fiber tip protective structure is a cap or ferrule fixed to a jacket or one of the buffer layers of the fiber.

3. A fiber tip protective structure as claimed in claim 1, wherein the cap or ferrule extends beyond the distal end of the fiber to provide a standoff between the fiber and a stone during a lithotripsy procedure.

4. A fiber tip protective structure as claimed in claim 1, wherein the ferrule or cap includes a transparent end section to which the ruler or scale lines are applied.

5. A fiber tip protective structure as claimed in claim 1, wherein the ruler or scale lines have alternating widths.

6. A fiber tip protective structure as claimed in claim 1, wherein the ruler or scale lines include a relatively wider band for extra visibility and fiber tip alignment.

7. A fiber tip protective structure as claimed in claim 1, wherein the ruler or scale lines are radio opaque markings visible under diagnostic imaging.

8. A fiber tip protective structure as claimed in claim 1, wherein the fiber tip protective structure includes a transparent end section to which the scale-indicating markings are applied.

9. A fiber tip protective structure as claimed in claim 8, wherein the scale-indicating markings are applied to an inside surface of or embedded within the transparent section.

10. A fiber tip protective structure that surrounds at least a distal end of a surgical laser fiber, the surgical laser fiber including at least a core, a cladding layer, and one or more buffer layers surrounding the core and cladding layer and extending a length of the fiber, at least one buffer layer being stripped at the distal end, the surgical laser fiber being inserted through a scope to a treatment site and the distal end of the surgical laser fiber being visible through the scope when the distal end is at the treatment site, wherein:
scale-indicating markings are applied to the fiber tip protective structure to enable a size of tissues or objects within a field of view of the scope to be determined, and
the scale-indicating markings are ruler or scale lines having alternating widths.

11. A fiber tip protective structure as claimed in claim 10, wherein the ruler or scale lines include a relatively wider band for extra visibility and fiber tip alignment.

12. A fiber tip protective structure as claimed in claim 1, wherein the fiber tip protective structure surrounds a forward firing fiber tip.

13. A fiber tip protective structure as claimed in claim 1, wherein the fiber tip protective structure surrounds a side firing fiber tip.

14. A fiber tip protective structure as claimed in claim 1, wherein the fiber tip protective structure is a soft tip, disposable tip, standoff tip, sleeve, sheath, or catheter.

15. A fiber tip protective structure that surrounds at least a distal end of a surgical laser fiber, the surgical laser fiber including at least a core, a cladding layer, and one or more buffer layers surrounding the core and cladding layer and extending a length of the fiber, at least one buffer layer being stripped at the distal end, the surgical laser fiber being inserted through a scope to a treatment site and the distal end of the surgical laser fiber being visible through the scope when the distal end is at the treatment site, wherein:
scale-indicating markings are applied to the fiber tip protective structure to enable a size of tissues or objects within a field of view of the scope to be determined, and
the scale-indicating markings are printed ruler or scale lines.

16. A fiber tip protective structure as claimed in claim 1, wherein the scale-indicating markings are applied to an outside surface of the fiber tip protective structure.

17. A fiber tip protective structure as claimed in claim 1, wherein the scale-indicating markings are radio opaque markings visible under diagnostic imaging.

18. A fiber tip protective structure as claimed in claim 10, wherein the scale-indicating markings are applied to an outside surface of the fiber tip protective structure.

19. A fiber tip protective structure as claimed in claim 15, wherein the scale-indicating markings are applied to an outside surface of the fiber tip protective structure.

\* \* \* \* \*